United States Patent
Ong

(10) Patent No.: US 7,223,443 B2
(45) Date of Patent: *May 29, 2007

(54) ANTIMICROBIAL CEMENTITIOUS COMPOSITION

(75) Inventor: Ivan Wei-Kang Ong, Charlotte, NC (US)

(73) Assignee: Microban Products Company, Huntersville, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 11/219,251

(22) Filed: Sep. 2, 2005

(65) Prior Publication Data

US 2006/0048671 A1 Mar. 9, 2006

Related U.S. Application Data

(60) Provisional application No. 60/606,950, filed on Sep. 3, 2004.

(51) Int. Cl.
*B05D 5/00* (2006.01)
*B05D 7/00* (2006.01)
*A01N 31/08* (2006.01)
*C04B 103/67* (2006.01)
*C04B 103/69* (2006.01)

(52) U.S. Cl. .................. 427/372.2; 106/15.05; 106/18.32; 106/18.33; 106/18.34; 106/18.35; 106/724; 106/725; 106/727; 106/783; 106/802; 106/808; 106/809; 427/256; 427/397.7; 427/403; 514/731

(58) Field of Classification Search ............. 106/15.05, 106/18.32, 18.33, 18.34, 18.35, 724, 725, 106/727, 802, 808, 809, 783; 427/256, 372.2, 427/397.7, 403; 514/731

See application file for complete search history.

(56) References Cited

U.S. PATENT DOCUMENTS

| | | | |
|---|---|---|---|
| 5,472,498 A * | 12/1995 | Stephenson et al. | 106/672 |
| 6,544,441 B2 * | 4/2003 | Wachtler et al. | 252/400.61 |
| 6,752,867 B1 * | 6/2004 | Kurihara et al. | 106/733 |
| 6,767,647 B2 * | 7/2004 | Swofford et al. | 428/537.7 |
| 6,777,103 B2 * | 8/2004 | Merkley et al. | 428/532 |

* cited by examiner

*Primary Examiner*—Anthony J. Green
(74) *Attorney, Agent, or Firm*—Cliff D. Weston

(57) ABSTRACT

An antimicrobial cementitious composition for imparting antimicrobial characteristics to cement comprises cement and an antimicrobial agent selected from the group consisting of an ortho-phenyl phenol or salt thereof, a tolyl diiodomethyl sulfone, a zinc pyrithione, an oxathiazine, an azole, a chlorothalonil, and a triazine diamine; combinations of agents also may be employed.

11 Claims, 15 Drawing Sheets

ANTIMICROBIAL CEMENTITIOUS COMPOSITION

CROSS-REFERENCE TO RELATED APPLICATION

This application claims priority from U.S. Ser. No. 60/606,950, filed on Sep. 3, 2004, the contents of which are incorporated herein for all purposes.

FIELD OF THE INVENTION

The present invention relates to antimicrobial cementitious compositions, and in particular to antimicrobial cementitious compositions and methods for producing same.

BACKGROUND OF THE INVENTION

Cementitious compositions have been used in the construction industry for years. Examples of cementitious compositions include concrete, mortar, grout, and stucco. Stucco is commonly used in the construction of buildings, particularly on the exterior of a building in lieu of vinyl siding. A framework such as paper or metal wire is affixed to a building, for example, and stucco is applied to the framework. Stucco is typically comprised of cement and inert materials such as sand and lime.

A common problem with a cementitious composition such as stucco is that it has a high pH when it is fresh or newly applied. A high pH (e.g., >9) intrinsically protects against microorganisms and will naturally protect the material from attack by fungi and other microorganisms. However, over time, the cementitious composition is gradually neutralized and an untreated cementitious composition loses this innate efficacy against microorganisms such as bacteria, algae, mold and fungus. Furthermore, stucco is porous and absorbs moisture, which is particularly attractive to microorganisms.

Others have attempted to add antimicrobial agents to cementitious compositions and to other components of cementitious compositions such as fibers. However, there are problems that have yet to be solved with known antimicrobial cementitious compositions. For example, the high pH of cementitious compositions places unique demands on the particular choice of an antimicrobial agent. Since the pH of a cured cementitious composition tends to remain very high even after it sets, the particular antimicrobial agent chosen must be very resistant to hydrolysis at the high pH. If the antimicrobial agent is susceptible to hydrolysis, then it would be most likely to be quickly degraded. Some antimicrobial agents such as triclosan are also particularly sensitive to the combination of high pH and ultraviolet light such that the antimicrobial agent causes yellowing when the two conditions are present. For example, U.S. Pat. No. 6,162,845 discloses the use of triclosan in fibers for blending with concrete and like materials.

Another problem with many known antimicrobial agents is that they disrupt the cure chemistry of a cementitious composition. For example, certain antimicrobial agents may be susceptible to coupling with impurities and will lead to possible color changes. Still another problem with many known antimicrobial agents is that they have poor solubility in a cementitious composition. The agents may leach out of the cementitious composition and, also as a result of poor solubility, cannot be homogeneously applied to the substrate.

BRIEF DESCRIPTION OF THE DRAWINGS

The antimicrobial cementitious composition described herein will become more fully understood from the detailed description and the accompanying drawings, wherein.

DETAILED DESCRIPTION OF THE PREFERRED EMBODIMENTS

Figure 1:
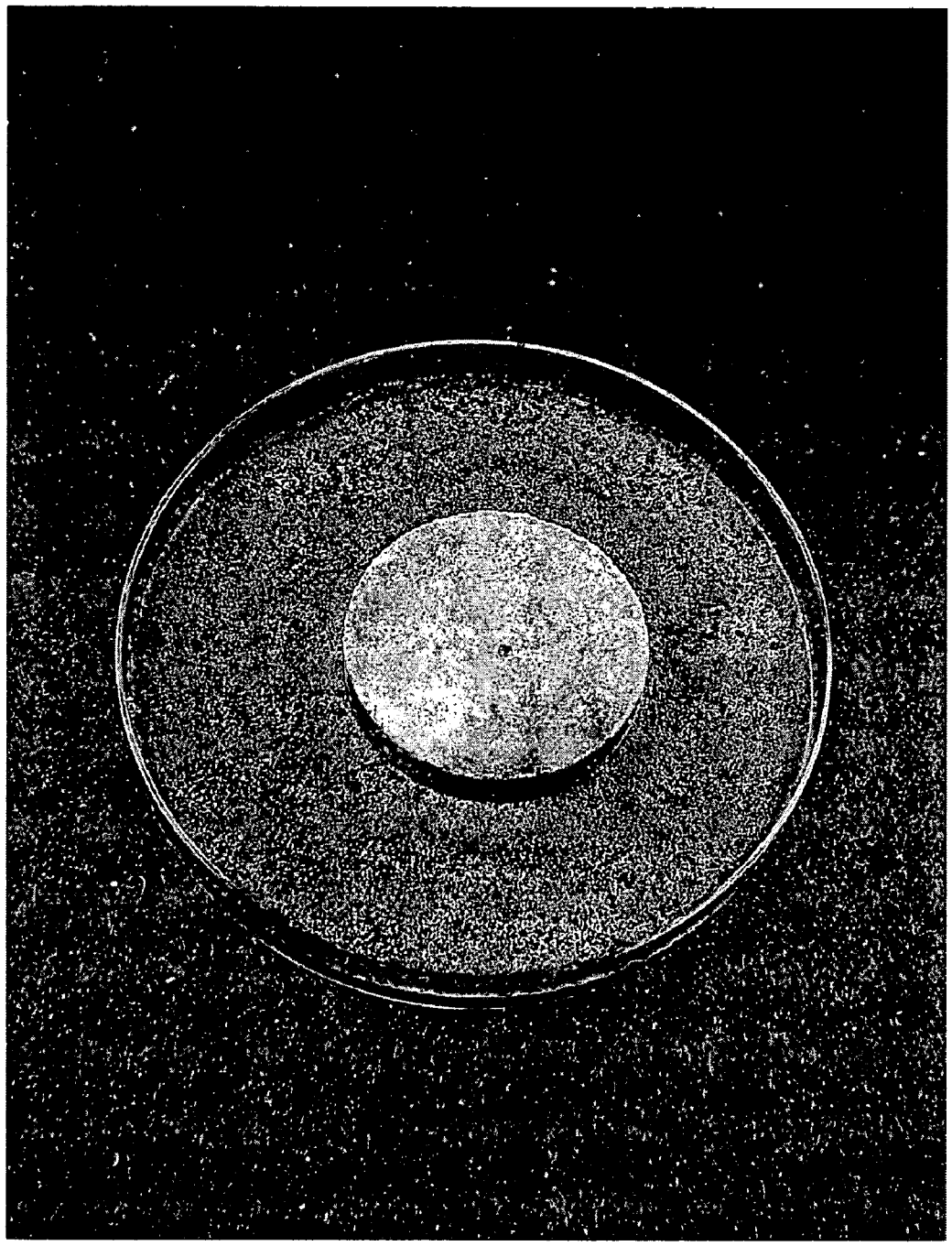
FIG. 1 is a photograph after inoculation with a fungal species of a cementitious composition sample that contains no antimicrobial agent.

The following description of the preferred embodiment(s) is merely exemplary in nature and is in no way intended to limit the antimicrobial cementitious composition, its application, or uses.

The term "antimicrobial" as used herein includes biostatic activity, i.e., where the proliferation of microbiological species is reduced or eliminated, and true biocidal activity where microbiological species are killed. Furthermore, the terms "microbe" or "antimicrobial" should be interpreted to specifically encompass bacteria and fungi as well as other single-celled organisms such as mold, mildew and algae.

The term "cement" as used herein refers to a commonly known building material comprising powdered materials which develop strong adhesive qualities when combined with water. Cement generally is a dry powder made of a mixture of calcined limestone, silica, alumina, lime, iron oxide, magnesia and clay, typically used with water and sand or gravel to make concrete and mortar.

The term "cementitious" as used herein refers to the presence of cement. A cementitious composition comprises cement but also may further comprise inert materials such as sand and lime. "Cement" as used herein may further comprise other additives such as stabilizers, durability enhancers, colorants, viscosity modifiers, and the like.

Examples of cementitious compositions include, but are not limited to, concrete, grout, mortar and stucco. A preferred cementitious composition is stucco, which typically is comprised of cement and sand. Stucco generally is commercially available in a premixed form.

The antimicrobial cementitious composition has antimicrobial activity and is comprised of cement and one or more antimicrobial agents. Antimicrobial agents suitable for use in the present composition include, but are not limited to, ortho-phenyl phenol (or salts thereof), zinc pyrithione, tolyl diiodomethyl sulfone, oxathiazine, chlorothalonil, azole, triazine diamine, and mixtures thereof.

Chlorothalonil or 2,4,5,6-Tetrachloroisophthalonitrile (CAS No. 1897-45-6) is commercially available under the trade name MICROBAN ADDITIVE M15™ (Microban Products Company, Huntersville, N.C).

As used herein the term "azoles" should be interpreted to include any of the "azole" antimicrobial agents known to those skilled the art. Preferred azoles include, but are not limited to, thiabendazole, propiconazole, tebuconazole, and mixtures thereof.

A preferred oxathiazine is bethoxazin commercially available under the trade name MICROBAN ADDITIVE GBF™ (Microban Products Company, Huntersville, N.C.).

Suitable triamine diamines include, but are not limited to, 1,3,5-triazine-2,4-diamine, cyclopropyl-N'-(1,1-dimethylethyl)-6-(methylthio)-1,3,5-triazine-2,4-diamine, commercially available as MICROBAN ADDITIVE IA1™ (Microban Products Company, Huntersville, N.C.).

A preferred ortho-phenyl phenol is sodium orthophenyl phenol (NaOPP) which is commercially available under the trade name MICROBAN ADDITIVE P2™ (Microban Products Company, Huntersville, N.C.).

For ease of discussion, the above chemicals are collectively referred to herein as "antimicrobial agents." One criterion in the selection of an antimicrobial agent as used in the practice of the present composition is that it be efficacious at commercially acceptable concentrations; in other words, that the efficacious agent concentration be commercially cost-permissive and not cause undue harm to the surface to which it is affixed or to the environment.

In one embodiment, an antimicrobial cementitious composition for imparting antimicrobial characteristics to cement comprises cement and an antimicrobial agent. The antimicrobial agent is preferably an ortho-phenyl phenol, a tolyl diiodomethyl sulfone, a zinc pyrithione, an oxathiazine, an azole, a chlorothalonil, a triazine diamine, or a mixture thereof.

In another embodiment, a method of making an antimicrobial cementitious composition is provided, comprising combining a quantity of an antimicrobial agent with cement to form an antimicrobial cementitious composition. The weight concentration of antimicrobial agent in the cementitious composition is preferably in a range from about 750 ppm to about 3000 ppm based upon the weight of the cementitious composition. The antimicrobial agent is preferably an ortho-phenyl phenol, a tolyl diiodomethyl sulfone, a zinc pyrithione, an oxathiazine, an azole, a chlorothalonil, a triazine diamine, or a mixture thereof.

In preferred embodiments, the combined weight concentration of the antimicrobial agent in the cementitious composition is in a range from about 750 ppm to about 3000 ppm based upon the weight of the cementitious composition. In preferred embodiments, the antimicrobial agent is present in the cementitious composition in a concentration range from about 750 ppm to about 3000 ppm. More preferred embodiments utilize a range from about 1000 ppm to about 3000 ppm.

A method for making an antimicrobial cementitious composition comprises the steps of combining a quantity of antimicrobial agent with cement to form an antimicrobial cementitious composition wherein the combined weight concentration of the antimicrobial agent in the cementitious composition is in a range from about 750 ppm to about 3000 ppm based upon the weight of the cementitious composition. In preferred embodiments, the cementitious composition is stucco. In preferred embodiments, the antimicrobial agent is added to cementitious composition to provide a final concentration in a range from about 750 ppm to about 3000 ppm. However, it is within the scope of the present method to use concentrations of antimicrobial agents greater than 3000 ppm.

The uniquely high pH of cementitious systems places unique demands on the particular choice of an antimicrobial agent. As the pH of a cured cementitious system tends to remain very high even after it sets, the particular antimicrobial agent chosen must be very resistant to hydrolysis at the high pH. If the antimicrobial agent is susceptible to hydrolysis, then it would be most likely be quickly degraded. Some antimicrobial agents such as triclosan are also particular sensitive to exposure to ultraviolet light such as from sunlight and high pH, and such antimicrobial agents will yellow when the two elements are present. As stated above, a preferred antimicrobial agent for use in the antimicrobial cementitious composition of the present disclosure is NaOPP. For example, NaOPP satisfactorily addresses this stability requirement as it has outstanding high pH stability.

NaOPP does not disrupt the cure chemistry of the cementitious composition and seems to have no effect on the setting time. Furthermore, NaOPP has the optimal combination of stability and solubility in the cementitious composition. It is not easily leached out of stucco and does not dissolve out of stucco at neutral to acidic pHs as its solubility in that range is very low. NaOPP is not degraded by neutral or acidic rain water.

While fresh cementitious/stucco compositions have a high intrinsic pH that will naturally protect the material from micro-organism attack, with time, the structure will gradually loose its intrinsic high pH due to atmospheric neutralization. Thus, due to its excellent combination of low leach and good stability, NaOPP is a preferred antimicrobial agent for use in the antimicrobial cementitious composition, as it is very easy to add to stucco as it dissolves rapidly into a slurry mix. Thus, the protection provided by NaOPP is expected to be very long lasting long after the intrinsic protection attenuates.

Stucco that is affixed to the exterior surface of a house is very usually painted. While possible fungicides in the paints protect the exterior surface, antimicrobial agents impart good overall protection to the entire stucco structure. There is still beneficial protection provided by the antimicrobial agents disclosed herein, as there might be moisture leach and fungal growth from within the wall outwards (e.g., water leaks and/or seepage through seams or flaws in the surface). Furthermore, the implemented antimicrobial agent is better retained within the cementitious composition, as the exterior paint coating acts as a barrier to the elements and possible leaching.

In a further embodiment, a method is disclosed for making an antimicrobial solid cementitious article. The method comprises affixing an antimicrobial cementitious composition as described above to a substrate, and dehydrating the composition so affixed. One representative example would include the affixation of stucco to a surface of a house or similar structure.

EXAMPLE 1

An 80 lb bag of TradeMix Pre-mix Sanded Stucco was obtained. NaOPP (MICROBAN ADDITIVE P2™) was added to the stucco dry mix at levels of 750 ppm (0.075%), 1500 ppm (0.15%) and 3000 ppm (0.3%), respectively, based upon the total weight of the dry mix and antimicrobial agent (excluding water). Each batch of dry mix and antimicrobial agent was 200 g. Water was added (32 g) according to packaging instructions, after which the mix was thoroughly mixed before being cast into round molds of approximately 1.5 inches in diameter. In addition, an untreated set of samples prepared according to packaging instructions was cast as controls for testing comparison.

After a 5-day air-cure, the samples were soaked in 0.1 M HCL for five days. The acid was replaced whenever the pH of the water rose above 5. The pH treatment was necessary as the intrinsic alkalinity in fresh-cast stucco would interfere with the fungal testing.

Following the neutralization treatment, the samples were reconditioned in water for two days and then plated against *Aspergillus niger* (a common household black mold) using the AATCC 30 Part III test. The AATCC 30 Part III test is an aggressive 7-day antifungal evaluation where the test samples are exposed to high levels of fungal spores and incubated under optimal conditions (elevated temperatures and humidity) for the spores to germinate.

At the end of the 7-day incubation period, the test plates were removed from the test chamber and the samples were evaluated for fungal attack and encroachment. The results of the evaluation are shown in FIGS. 1-4.

FIG. 1 is a photograph of an untreated stucco sample that was exposed to *Aspergillus niger*. The fungus appears to have encroached upon the edges of the stucco sample and shows initial signs of growth up the sides of the sample. The untreated sample appears to offer little resistance to fungal attack.

Figure 2:
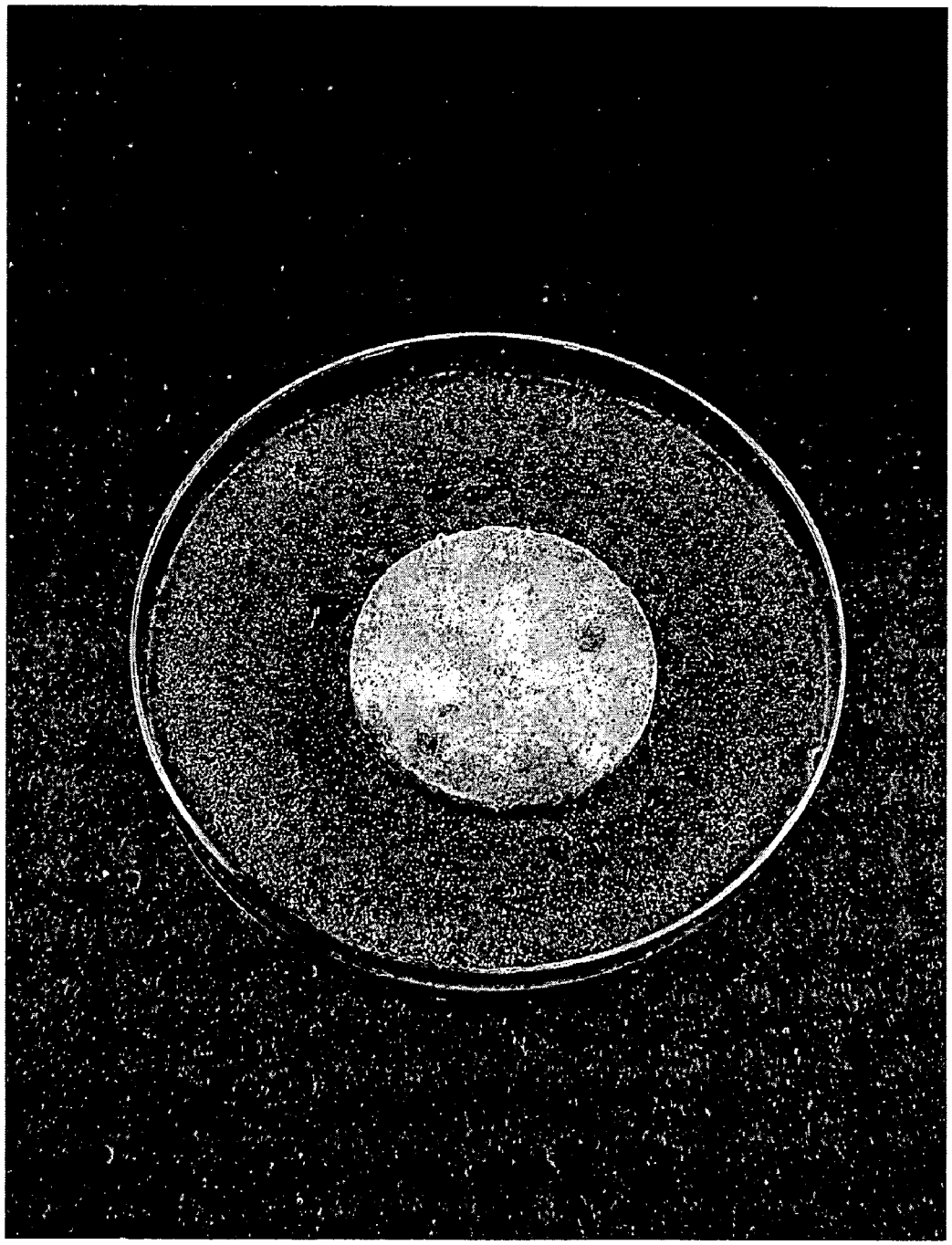
FIG. 2 is a photograph after inoculation with a fungal species of a cementitious composition sample that contains an antimicrobial agent.

FIG. 2 is a photograph of a stucco sample at 750 ppm of NaOPP. At 750 ppm, the stucco sample appears to offer minimal resistance to fungal attack.

Figure 3:
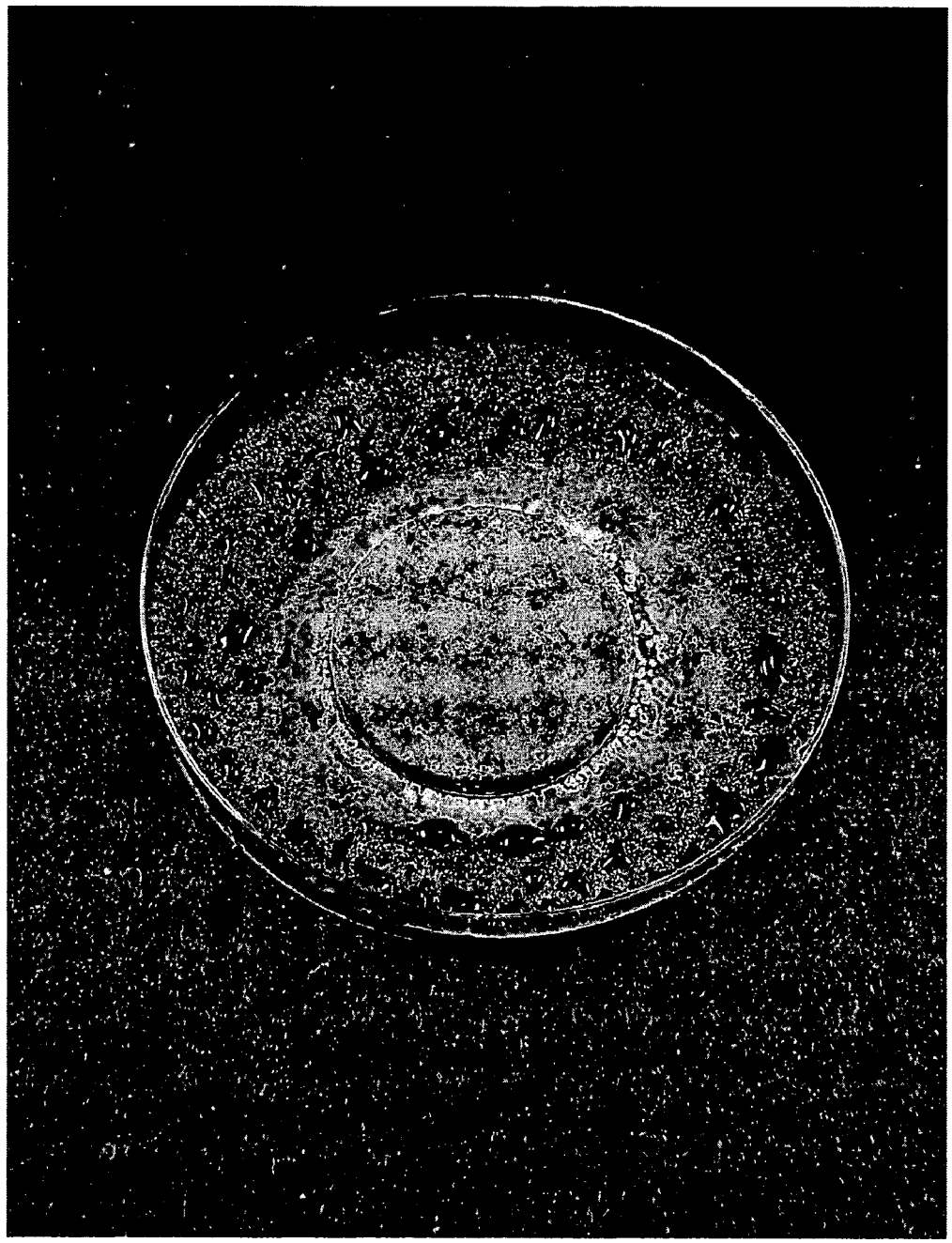
FIG. 3 is a photograph after inoculation with a fungal species of a cementitious composition sample that contains an antimicrobial agent.

FIG. 3 is a photograph of a stucco sample at 1500 ppm of NaOPP. At 1500 ppm, the stucco sample appears to offer significant disruption to fungal encroachment in its immediate vicinity. The lighter contrast of the fungal lawn is indicative of a hostile environment to fungal propagation.

Figure 4:
FIG. 4 is a photograph after inoculation with a fungal species of a cementitious composition sample that contains an antimicrobial agent.

FIG. 4 is a photograph of a stucco sample at 3000 ppm of NaOPP. At 3000 ppm, the stucco sample appears to offer even more significant disruption to fungal encroachment in its immediate vicinity.

EXAMPLE 2

An 80 lb bag of TradeMix Pre-Mix Sanded Stucco was obtained. NaOPP (MICROBAN ADDITIVE P2™) was added to the mix at a level of 1000 ppm (0.1%), based upon the total weight of the dry mix and antimicrobial agent (excluding water). Each batch of dry mix and antimicrobial agent was 200 g. Water was added (32 g) to the stucco mix according to packaging instructions. After the water was added, the mix was thoroughly mixed before being cast into round molds of approximately 1.5 inches in diameter. Additionally, an untreated stucco sample was cast as a control for testing comparison.

After a five day air-cure, the samples were soaked in 0.1 M HCl for five days to remove residual alkalinity. Following the neutralization treatment, the samples were reconditioned in water for two days and then plated against *Aspergillus niger* using the AATCC 30 Part III test. At the end of the incubation period, the test plates were removed from the test chamber, and the samples were evaluated for fungal attack and encroachment. The results of the evaluation are shown in FIGS. 5 and 6.

Figure 5A:
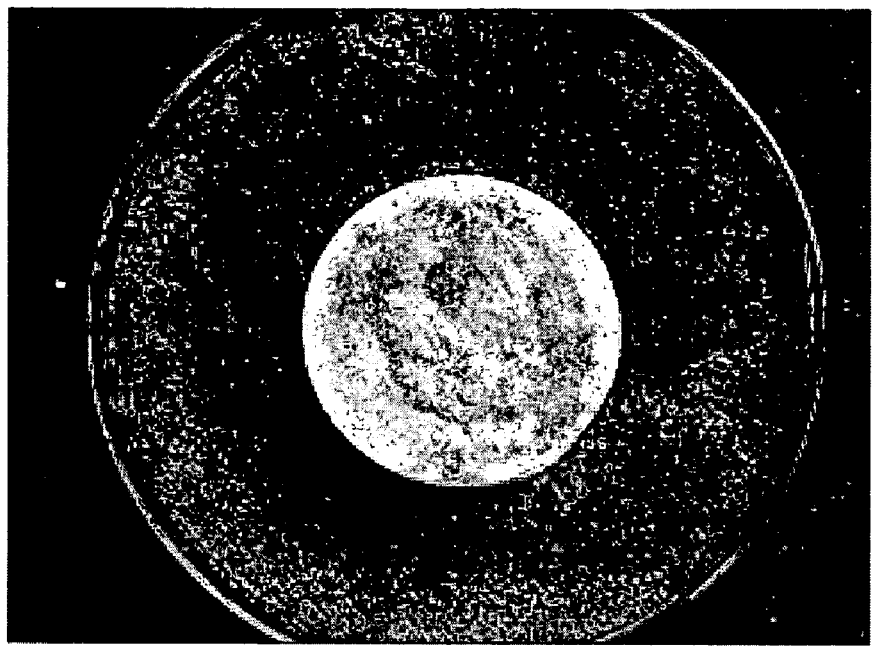
FIGS. 5A-5B are photographs after inoculation with a fungal species of both a cementitious composition sample with no antimicrobial agent and a cementitious composition sample that contains an antimicrobial agent, respectively.
Figure 5B:
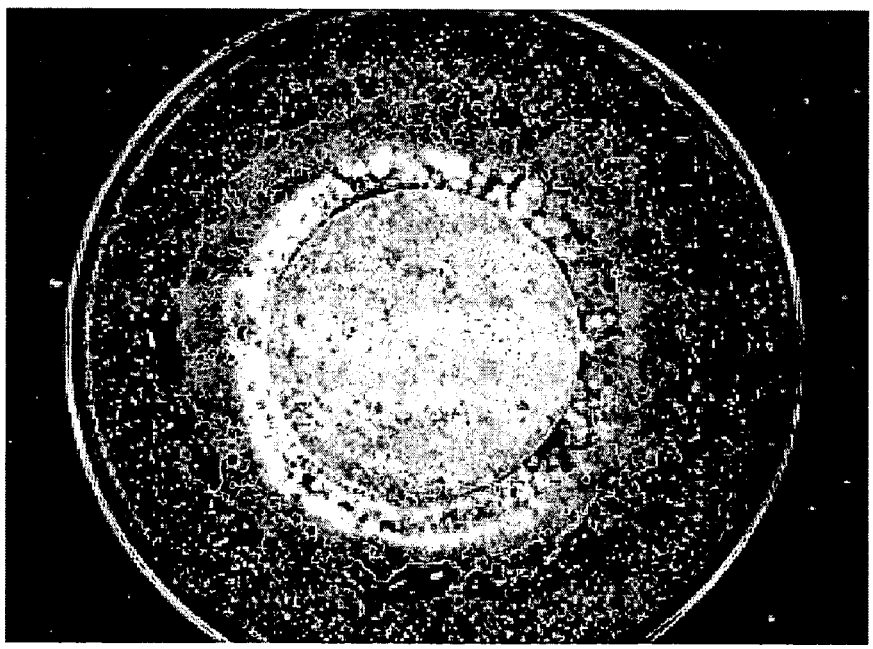

FIGS. 5A-5B are photographs comparing an untreated stucco control sample (FIG. 5A) and a stucco sample treated with 1000 ppm NaOPP (FIG. 5B). The control stucco sample shows fungal lawn all the way to the sample edge. The stucco sample treated with 1000 ppm NaOPP shows disruption of fungal lawn around the sample. The white mottled structure of the *Aspergillus niger* around the sample treated with 1000 ppm NaOPP clearly indicates that the fungal organism is under stress and unable to produce the darkly-colored fruiting structures for reproduction. It is also worthy of note that the top surface of the sample treated with 1000 ppm NaOPP is extremely clean as compared to the top surface of the untreated sample.

Figure 6:
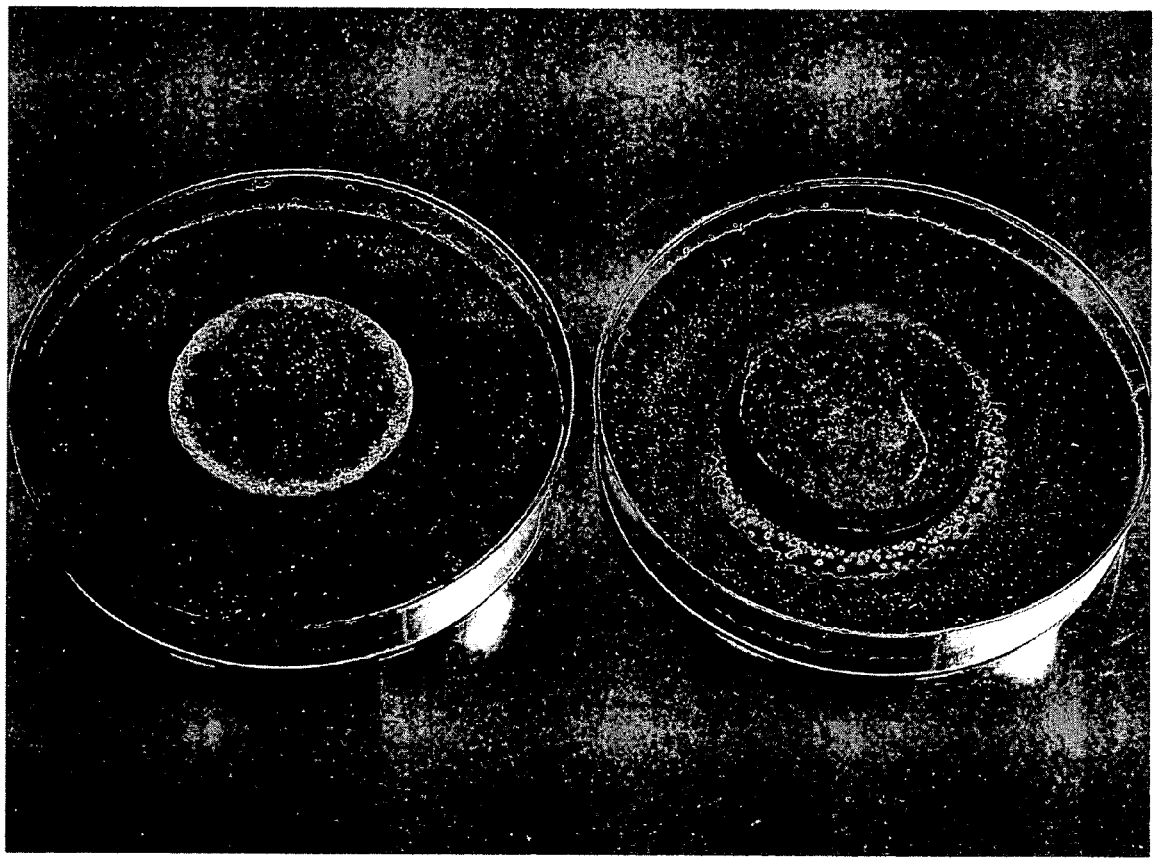
FIG. 6 is a photograph of another view of the samples of FIGS. 5A-5B.

FIG. 6 is a photograph of another view of the samples of FIG. 5 with the untreated sample (control) on the left and the sample treated with 1000 ppm NaOPP on the right.

EXAMPLE 3

The stucco samples were prepared and cured as in Example 1. Antimicrobial agents were each added to the mix at levels of 750 ppm, 1500 ppm, and 3000 ppm, respectively, based upon the total weight of the dry mix and antimicrobial agent (excluding water).

After air-curing, the samples were soaked in 0.1 M HCl for five days and then plated against *Aspergillus niger* using the AATCC Test Method 30 Part III test. At the end of the incubation period, the test plates were removed from the test chamber, and the samples were evaluated for fungal attack and encroachment. The antimicrobial agent tested and the results of the evaluation are shown in FIGS. 7-15.

Mold was observed to grow freely in the control plate medium and on the cementitious sample. A small zone of inhibition (ZI) was observed around a cementitious sample treated at 750 ppm of diiodomethyl-p-tolylsulfone, commercially available as MICROBAN ADDITIVE AF™ from Microban Products Company. Somewhat larger inhibitory zones were seen around the cementitious samples treated with 1500 ppm of diiodomethyl-p-tolylsulfone and with 3000 ppm of diiodomethyl-p-tolylsulfone.

Figure 7:
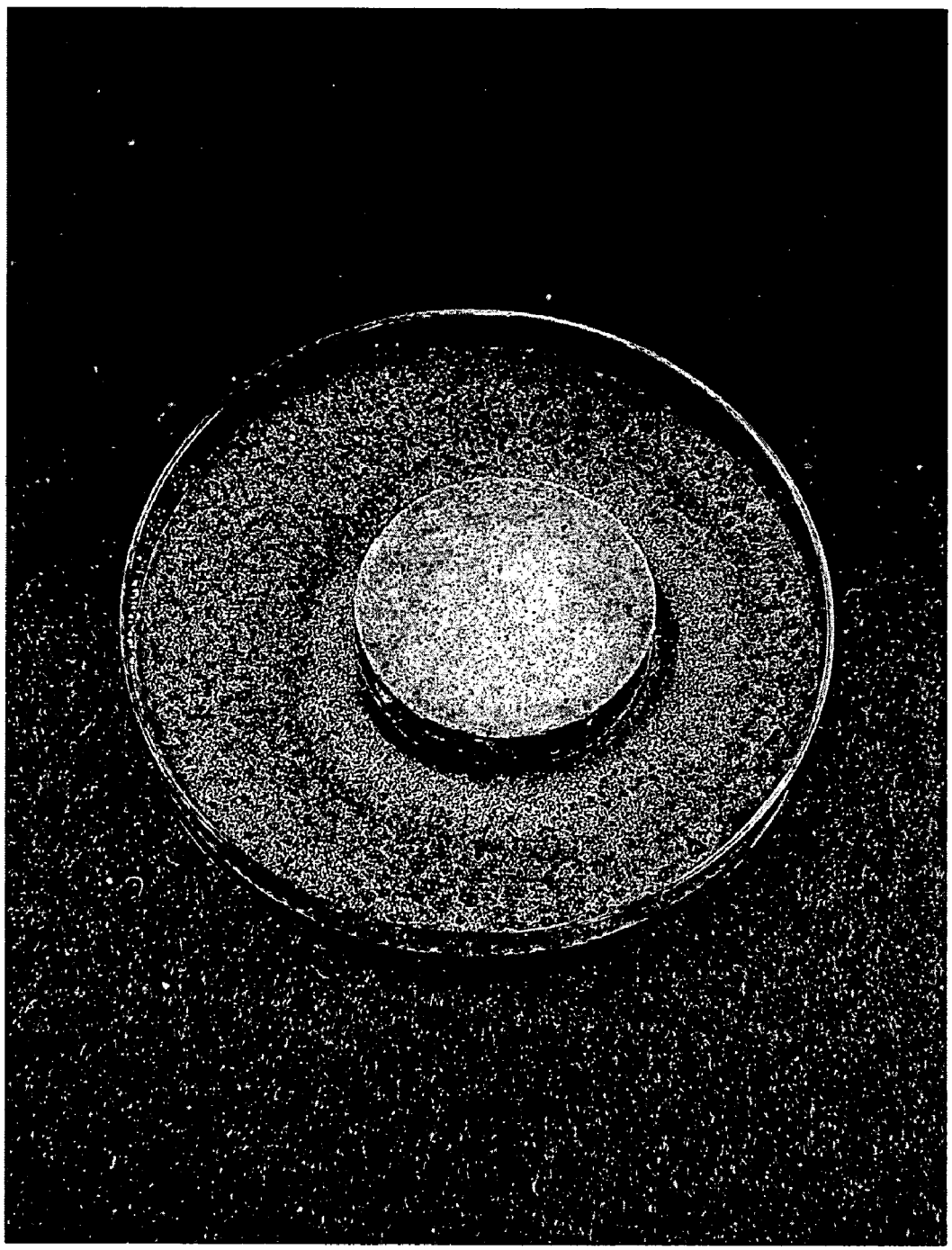
FIGS. 7-15 are photographs after inoculation with a fungal species of cementitious composition samples that contains one or more antimicrobial agents.
Figure 8:
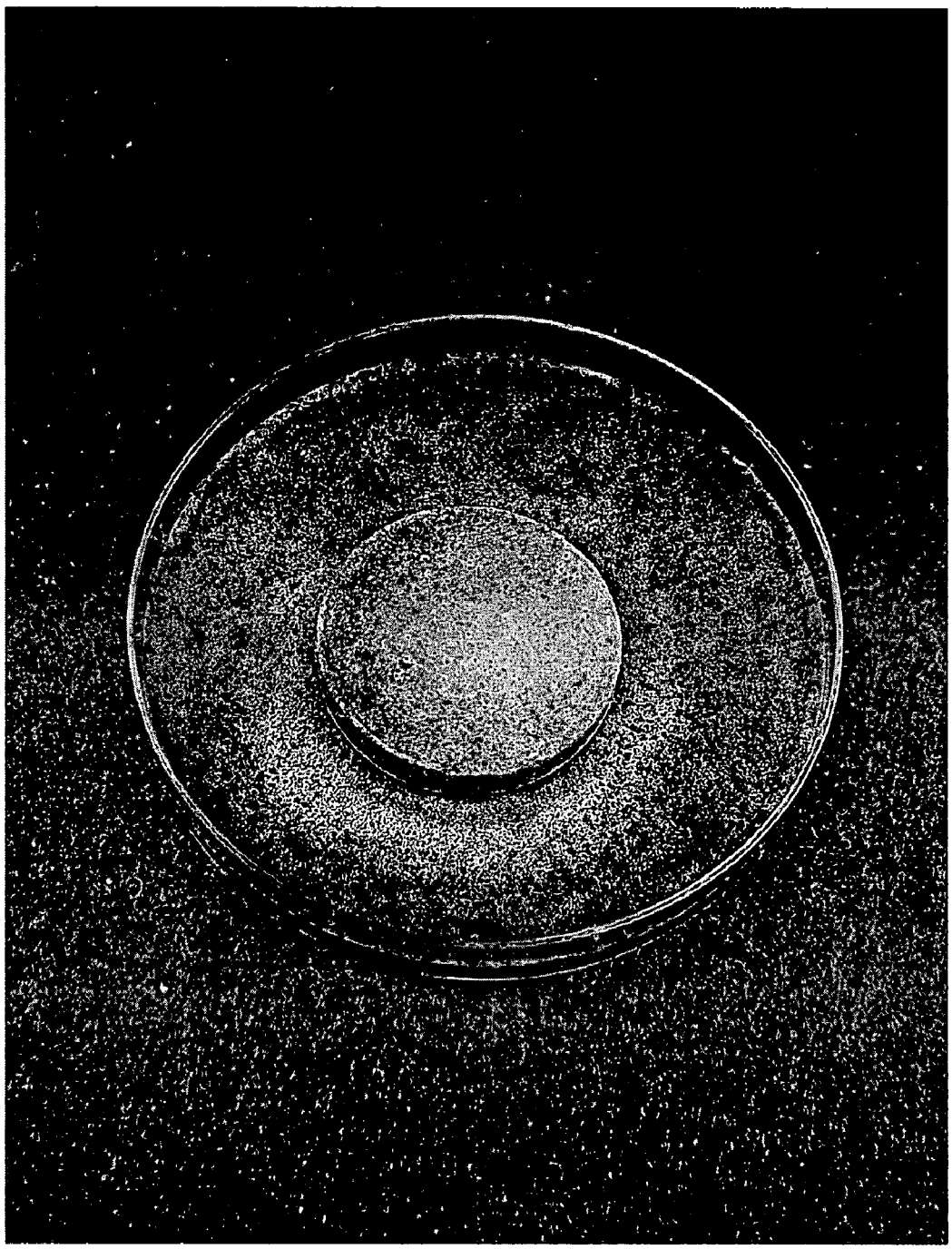
Figure 9:
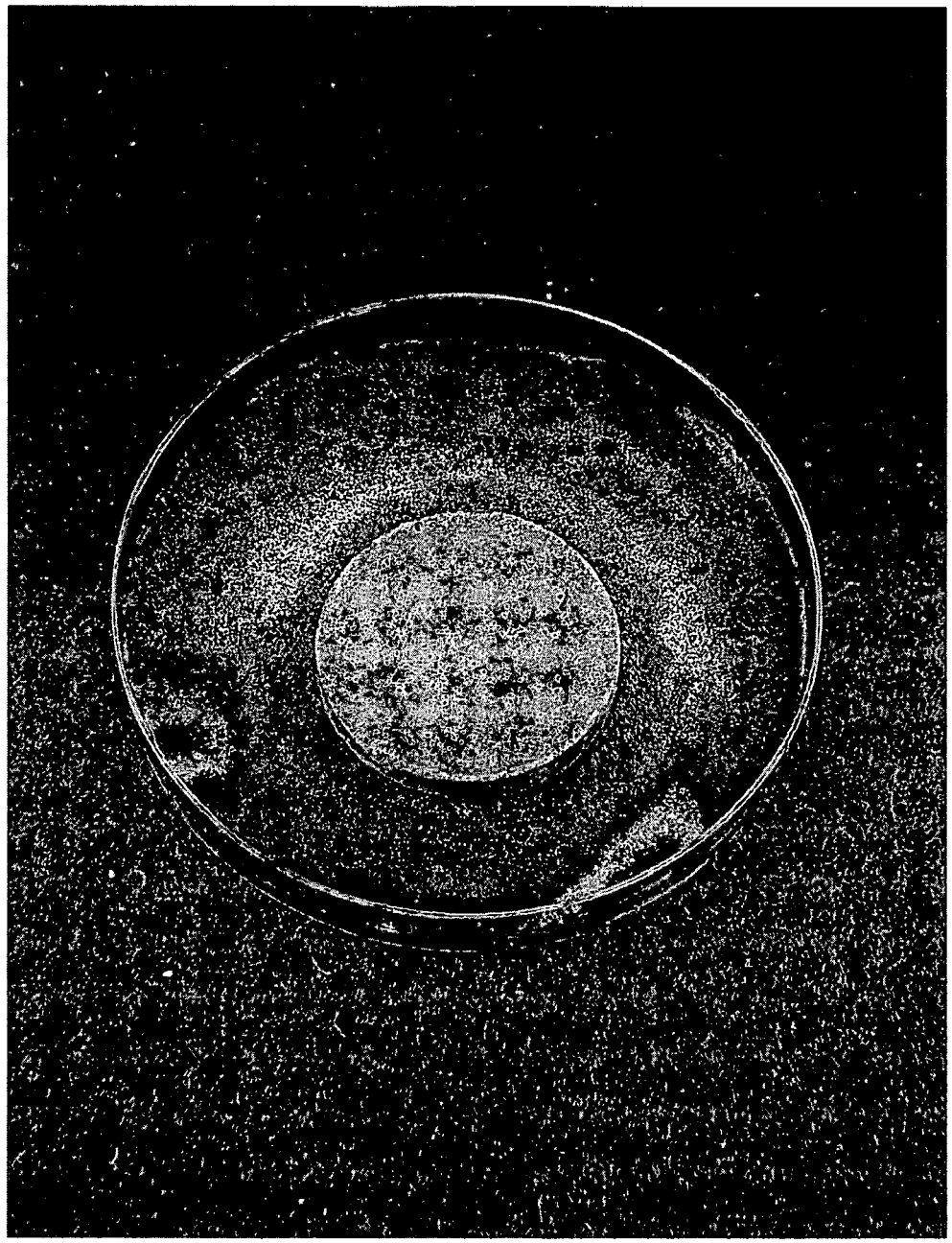

FIG. 7 is a photograph of a stucco sample treated with 750 ppm of zinc pyrithione, commercially available as MICROBAN ADDITIVE ZO1™ from Microban Products Company. FIG. 8 is a photograph of a stucco sample treated with 1500 ppm of zinc pyrithione. FIG. 9 is a photograph of a stucco sample treated with 3000 ppm of zinc pyrithione.

A zone of inhibition can be observed peripheral to the cementitious samples plated in FIGS. 7-9, showing efficacy of incorporated zinc pyrithione in preventing fungal growth.

The following agents were used to treat cementitious stucco samples: bethoxazin, commercially available as MICROBAN ADDITIVE GBF™, at 750 ppm, 1500 ppm, and 3000 ppm; chlorothalonil, commercially available as MICROBAN ADDITIVE M15™, at 750 ppm and 1500 ppm; and chlorothalonil, commercially available as MICROBAN ADDITIVE M15™, at 3000 ppm. These experimental plates were seen to have zones of inhibition surrounding the cementitious samples.

Figure 10:
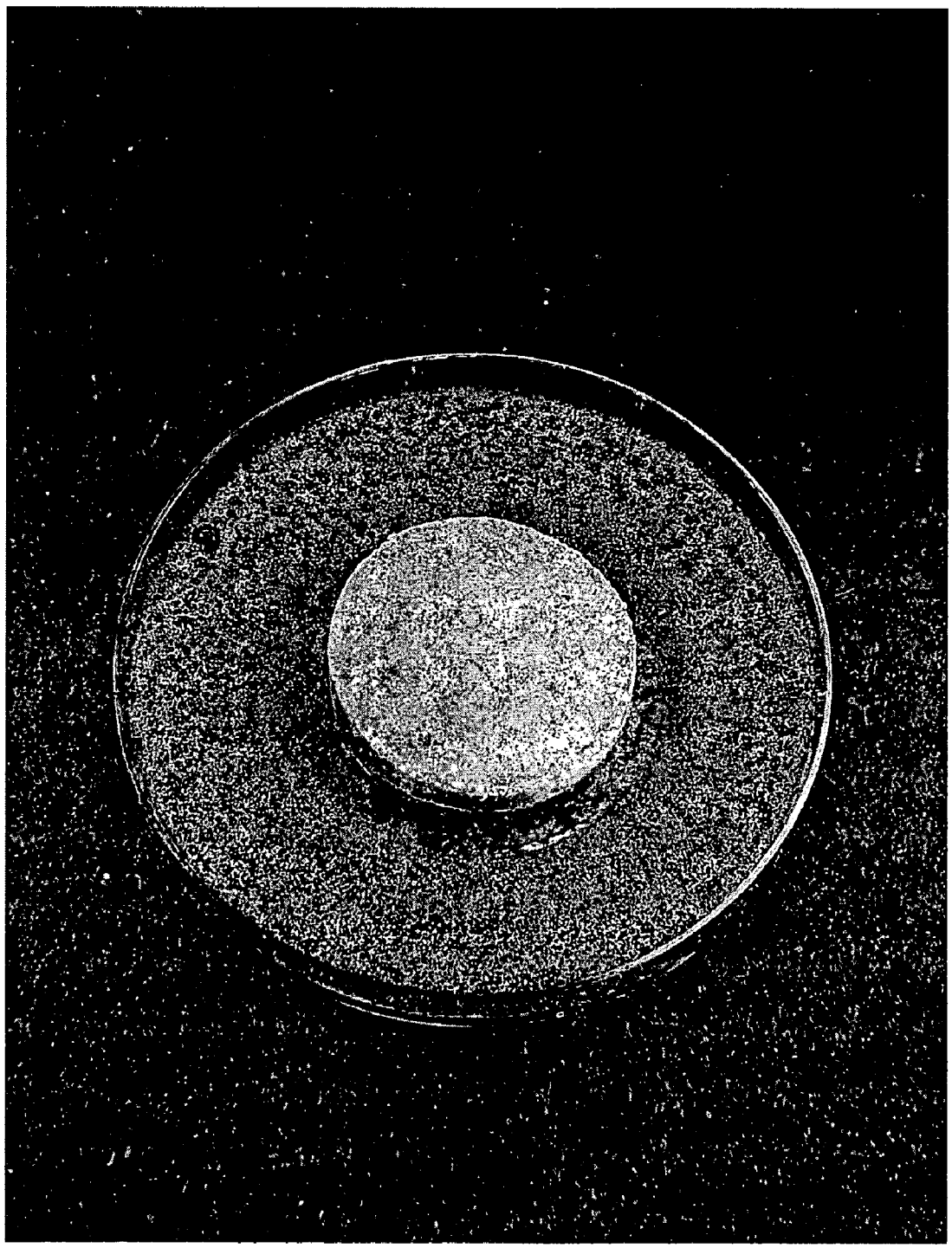
Figure 11:
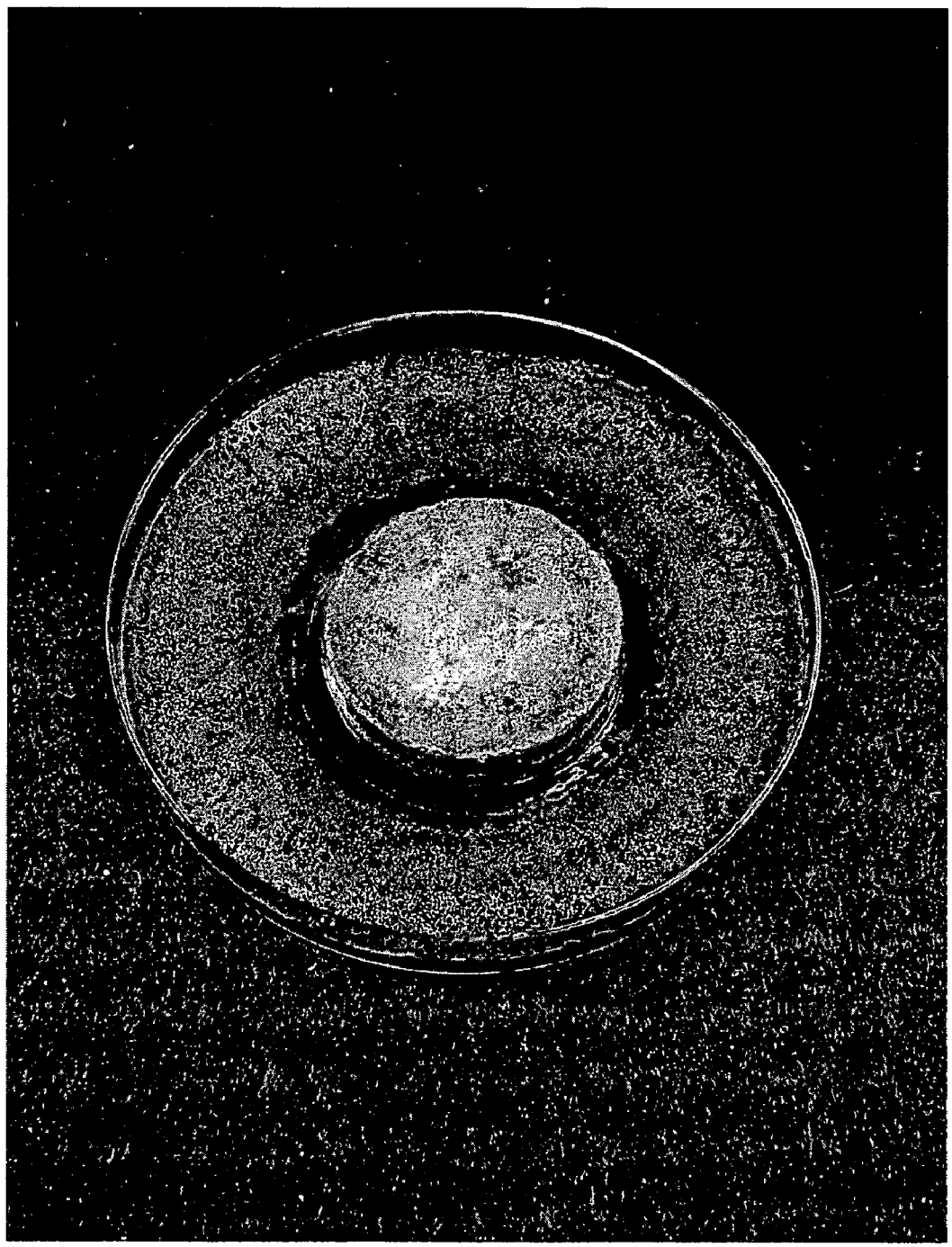
Figure 12:
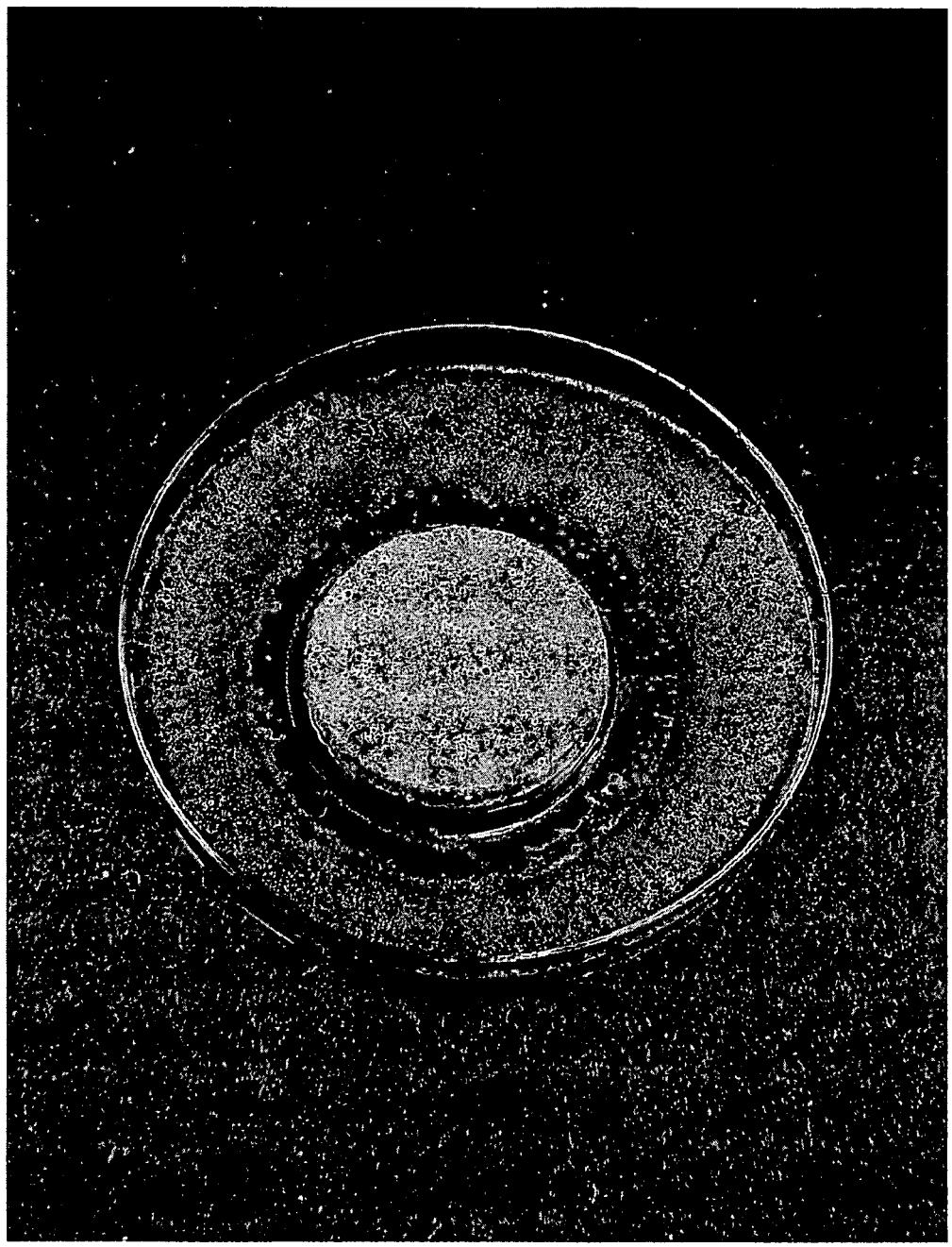
Figure 13:
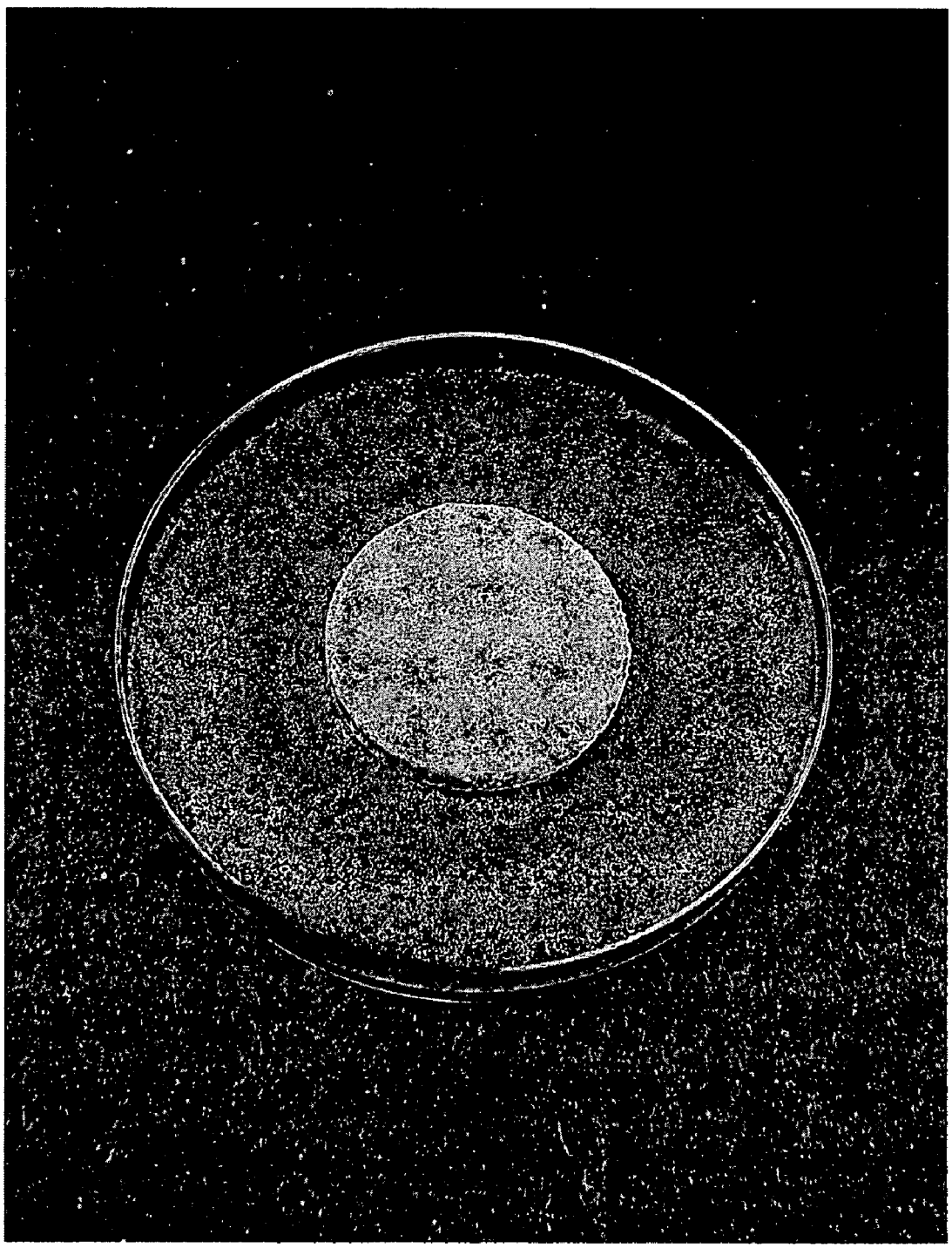
Figure 14:
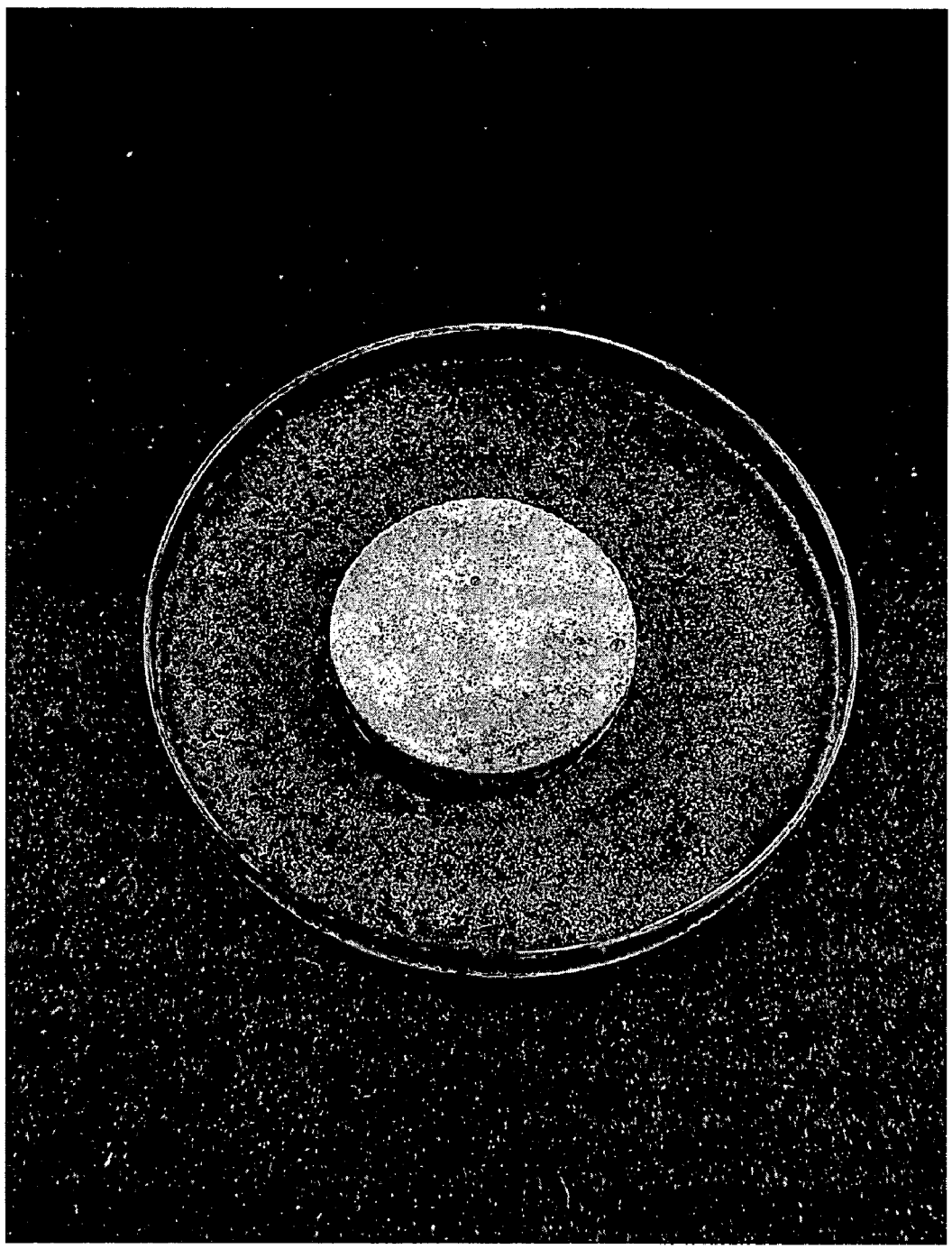
Figure 15:
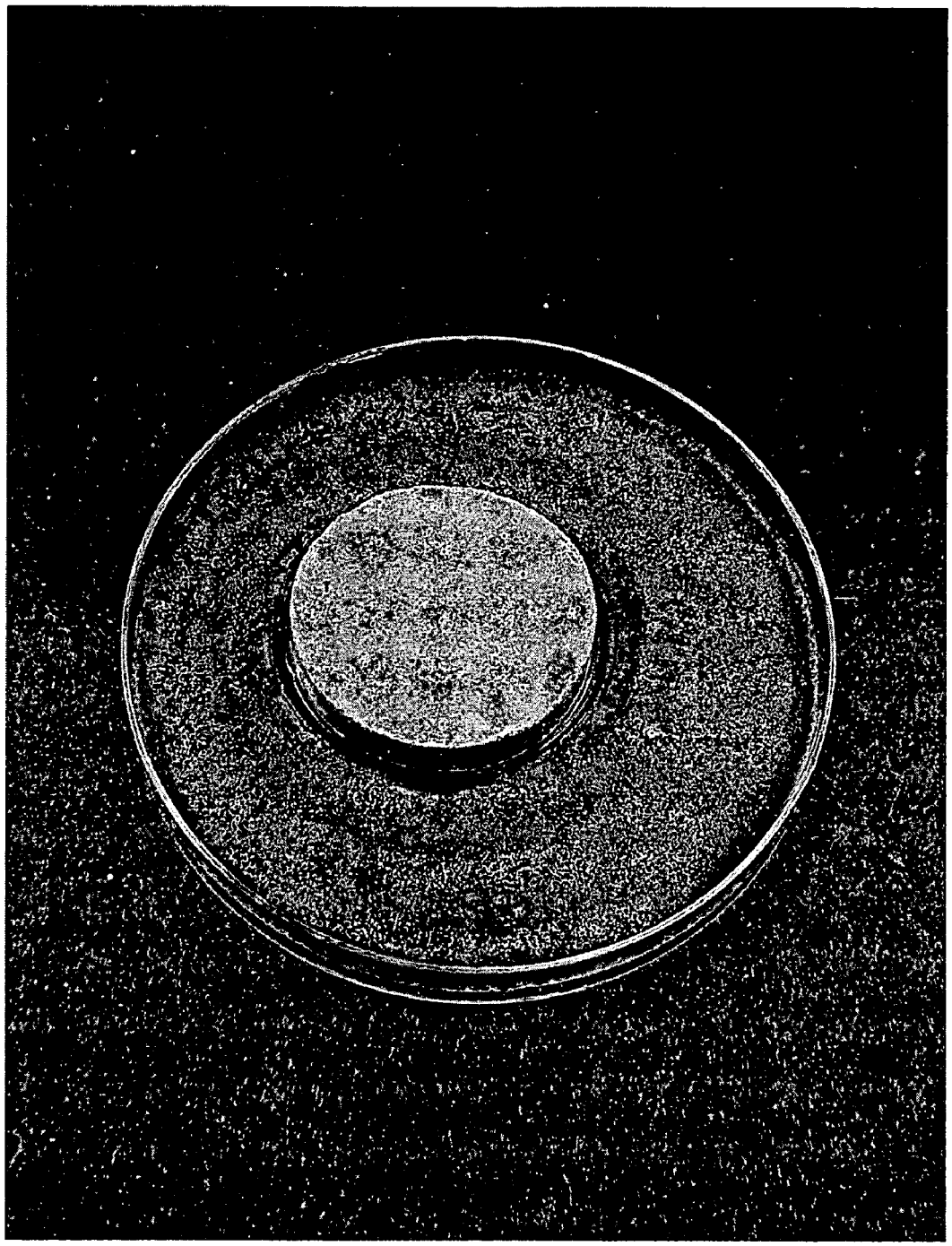

Combinations of antimicrobial agents also can be efficacious in cementitious compositions. FIG. 10 is a photograph of a stucco sample treated with 750 ppm of a 1:1 composition of bethoxazin, commercially available as MICROBAN ADDITIVE GBF™, and tebuconazole, commercially available as MICROBAN ADDITIVE TZ1™. FIG. 11 is a photograph of a stucco sample treated with 1500 ppm of a 1:1 composition of bethoxazin and tebuconazole. FIG. 12 is a photograph of a stucco sample treated with 3000 ppm of a 1:1 composition of bethoxazin and tebuconazole. FIG. 13 is a photograph of a stucco sample treated with 750 ppm of a 1:1 composition of bethoxazin, commercially available as MICROBAN ADDITIVE GBF™, and thiabendazole, commercially available as MICROBAN ADDITIVE IF1™ from Microban Products Company. FIG. 14 is a photograph of a stucco sample treated with 1500 ppm of a 1:1 composition of bethoxazin and thiabendazole. FIG. 15 is a photograph of a stucco sample treated with 3000 ppm of a 1:1 composition of bethoxazin and thiabendazole. These combinations of agents also show efficacy.

It will therefore be readily understood by those persons skilled in the art that the present composition and methods are susceptible of broad utility and application. Many embodiments and adaptations other than those herein described, as well as many variations, modifications and equivalent arrangements, will be apparent from or reasonably suggested to one of ordinary skill by the present disclosure and the foregoing description thereof, without departing from the substance or scope thereof. Accordingly, while the present composition and methods have been described herein in detail in relation to its preferred embodiment, it is to be understood that this disclosure is only illustrative and exemplary and is made merely for purposes of providing a full and enabling disclosure. The foregoing disclosure is not intended or to be construed to limit or otherwise to exclude any such other embodiments, adaptations, variations, modifications and equivalent arrangements.

What is claimed is:

1. A method for making an antimicrobial solid cementitious article, comprising:
   affixing an antimicrobial cementitious composition to a substrate, said antimicrobial cementitious composition including ortho-phenyl phenol; and
   dehydrating said affixed composition.

2. The method of claim 1 wherein the ortho-phenyl phenol is present in an amount at least from about 750 ppm to about 3000 ppm based on the weight of the cementitious composition.

3. The method of claim 1 wherein the ortho-phenyl phenol is sodium ortho-phenyl phenol.

4. The method of claim 1 wherein the cementitious composition is stucco.

5. The method of claim 1 wherein the antimicrobial cementitious composition further includes an antimicrobial agent selected from the group consisting of a tolyl diiodomethyl sulfone, a zinc pyrithione, an oxathiazine, a chlorothalonil, and a triazine diamine.

6. The method of claim 1 wherein the antimicrobial cementitious composition is selected from the group consisting of a concrete composition, a mortar composition, a grout composition, and a stucco composition.

7. The method of claim 1 wherein the antimicrobial cementitious composition is a stucco composition.

8. The method of claim 1 wherein the antimicrobial cementitious composition is in a liquid state.

9. The method of claim 1 wherein the antimicrobial cementitious composition is in a solid state.

10. The method of claim 9 wherein the antimicrobial cementitious composition is a powdered solid.

11. The method of claim 1 wherein the substrate is a substantially vertically oriented substrate.

* * * * *